US00PP24503P2

(12) United States Plant Patent
Sakazaki

(10) Patent No.: US PP24,503 P2
(45) Date of Patent: May 27, 2014

(54) *CALIBRACHOA* PLANT NAMED 'USCAL08501'

(50) Latin Name: ***Calibrachoa* sp.**
Varietal Denomination: USCAL08501

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 68 days.

(21) Appl. No.: 13/507,517

(22) Filed: Jul. 5, 2012

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Susan McCormick Ewoldt
(74) *Attorney, Agent, or Firm* — C. A. Whealy

(57) ABSTRACT

A new and distinct cultivar of *Calibrachoa* plant named 'USCAL08501', characterized by its upright, outwardly spreading to trailing and mounding plant habit; freely branching growth habit; dense and bushy appearance; early and freely flowering habit; dark red-colored flowers with large dark purple-colored centers and venation and yellow green-colored throats; and good garden performance.

1 Drawing Sheet

Botanical designation: *Calibrachoa* sp.
Cultivar denomination: 'USCAL08501'.

BACKGROUND OF THE INVENTION

The present invention relates to a new and distinct cultivar of *Calibrachoa* plant, botanically known as *Calibrachoa* sp. and hereinafter referred to by the name 'USCAL08501'.

The new *Calibrachoa* plant is a product of a planned breeding program conducted by the Inventor in Higashiomi, Shiga, Japan and Bonsall, Calif. The objective of the breeding program is to create new *Calibrachoa* plants with uniform plant habit, freely branching growth habit, unique flower coloration and good garden performance.

The new *Calibrachoa* plant originated from a cross-pollination made by the Inventor on May 6, 2009 in Higashiomi, Shiga, Japan of a proprietary seedling selection of *Calibrachoa* sp. identified as code name 07C557-02, not patented, as the female, or seed, parent with a proprietary seedling selection of *Calibrachoa* sp. identified as code name 09CJ12, not patented, as the male, or pollen, parent. The new *Calibrachoa* plant was discovered and selected by the Inventor as a single flowering plant within the progeny of the stated cross-pollination in a controlled environment in Bonsall, Calif. on May 27, 2010.

Asexual reproduction of the new *Calibrachoa* plant by terminal cuttings in a controlled environment in Bonsall, Calif. since May 28, 2010 has shown that the unique features of this new *Calibrachoa* plant are stable and reproduced true to type in successive generations.

SUMMARY OF THE INVENTION

Plants of the new *Calibrachoa* have not been observed under all possible environmental conditions and various cultural practices. The phenotype may vary somewhat with variations in environmental conditions such as temperature and light intensity without, however, any variance in genotype.

The following traits have been repeatedly observed and are determined to be the unique characteristics of 'USCAL08501'. These characteristics in combination distinguish 'USCAL08501' as a new and distinct *Calibrachoa* plant:

1. Upright, outwardly spreading to trailing and mounding plant habit.
2. Freely branching growth habit; dense and bushy appearance.
3. Early and freely flowering habit.
4. Dark red-colored flowers with large dark purple-colored centers and venation and yellow green-colored throats.
5. Good garden performance.

The new *Calibrachoa* plant can be compared to plants of the female parent selection. Plants of the new *Calibrachoa* differ primarily from plants of the female parent selection in flower color as plants of the female parent selection have red orange-colored flowers with yellow-colored centers.

The new *Calibrachoa* plant can be compared to plants of the male parent selection. Plants of the new *Calibrachoa* differ primarily from plants of the male parent selection in flower color as plants of the male parent selection have purple red-colored flowers with dark purple-colored centers.

Plants of the new *Calibrachoa* can be compared to plants of the Calibrachoa 'USCAL84704', disclosed in U.S. Plant Pat. No. 23,231. In side-by-side comparisons conducted in Bonsall, Calif., plants of the new *Calibrachoa* differed primarily from plants of 'USCAL84704' in flower color as plants of 'USCAL84704' had dark violet-colored flowers with dark purple-colored centers and yellow-colored throats.

Plants of the new *Calibrachoa* can be compared to plants of the *Calibrachoa* 'USCAL66501', disclosed in U.S. Plant Pat. No. 22,942. In side-by-side comparisons conducted in Bonsall, Calif., plants of the new *Calibrachoa* differed primarily from plants of 'USCAL66501' in flower color as plants of 'USCAL66501' had coral red-colored flowers with greyed purple-colored centers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet comprises a side perspective view of a typical flowering plant of 'USCAL08501' grown in a container.

The photograph at the top of the sheet is a close-up view of typical flowers of 'USCAL08501'.

DETAILED BOTANICAL DESCRIPTION

The aforementioned photographs and following observations, measurements and values describe plants grown during the spring in 25.4-cm containers in a polyethylene-covered greenhouse and finished in an outdoor nursery in Bonsall, Calif. During the production of the plants, day temperatures averaged 24° C. and night temperatures averaged 18° C. Plants were pinched four times and were 32 weeks old when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCAL08501'.

Parentage:

*Female, or seed, parent*.—Proprietary seedling selection of *Calibrachoa* sp. identified as code name 07C557-02, not patented.

*Male, or pollen, parent*.—Proprietary seedling selection of *Calibrachoa* sp. identified as code number 09CJ12, not patented.

Propagation:

*Type*.—By terminal cuttings.

*Time to initiate roots, summer*.—About four days at temperatures ranging from 17° C. to 29° C.

*Time to initiate roots, winter*.—About six days at temperatures ranging from 17° C. to 21° C.

*Time to produce a rooted plant, summer*.—About 22 days at temperatures ranging from 17° C. to 29° C.

*Time to produce a rooted plant, winter*.—About 25 days at temperatures ranging from 17° C. to 21° C.

*Root description*.—Medium in thickness, fibrous; white in color.

*Rooting habit*.—Freely branching; medium density.

Plant description:

*Plant and growth habit*.—Upright, outwardly spreading to trailing and mounding plant habit; freely branching habit with about 14 primary lateral branches each with about multiple secondary lateral branches; pinching enhances branching; moderately vigorous, dense and bushy growth habit.

*Plant height*.—About 27 cm.

*Plant diameter*.—About 34 cm by 66 cm.

Lateral branch description:

*Length*.—About 41 cm.

*Diameter*.—About 3 mm.

*Internode length*.—About 1.8 cm.

*Strength*.—Strong.

*Aspect*.—Initially upright to outwardly spreading to trailing.

*Texture*.—Pubescent.

*Color*.—Close to 145B.

Foliage description:

*Arrangement*.—Before flowering, alternate; after flowering, opposite; leaves simple.

*Length*.—About 3.2 cm.

*Width*.—About 1.4 cm.

*Shape*.—Elliptical to obelliptical.

*Apex*.—Obtuse.

*Base*.—Attenuate.

*Margin*.—Entire.

*Texture, upper and lower surfaces*.—Pubescent.

*Venation pattern*.—Pinnate; arcuate.

*Color*.—Developing leaves, upper surface: Close to 138A. Developing leaves, lower surface: Close to 138B. Fully expanded leaves, upper surface: Close to N137B; venation, close to 147B. Fully expanded leaves, lower surface: Close to 147B; venation, close to 147C.

*Petiole*.—Length: About 3 mm. Diameter: About 2 mm. Texture, upper and lower surfaces: Pubescent. Color, upper and lower surfaces: Close to 147C.

Flower description:

*Flower arrangement and habit*.—Single salverform flowers arising from leaf axils; freely flowering habit with usually about 19 open flowers per lateral branch; flowers face upright and outwardly.

*Fragrance*.—None detected.

*Natural flowering season*.—Early flowering habit, plants of the new *Calibrachoa* begin flowering about six weeks after planting; plants flower continuously from spring though the autumn in Southern California.

*Flower longevity*.—Individual flowers last about four to five days on the plant; flowers persistent.

*Flower diameter*.—About 3.3 cm.

*Flower length* (*height*).—About 2.6 cm.

*Flower throat diameter*.—About 4 mm by 8 mm.

*Flower tube length*.—About 1.5 cm.

*Flower tube diameter, base*.—About 2 mm.

*Flower buds*.—Shape: Elongated oblong to obdeltoid. Length: About 2.2 cm. Diameter: About 7 mm. Color: Close to 201C.

*Corolla*.—Arrangement: Five fused petals opening into a flared trumpet. Petal lobe length (from throat): About 1.5 cm. Petal lobe width: About 1.7 cm. Petal shape: Roughly obcordate. Petal apex: Cordate to rounded. Petal margin: Entire. Petal texture, upper surface: Smooth, glabrous; velvety. Petal texture, lower surface: Smooth, mostly glabrous with a few hairs along the veins. Throat texture: Smooth, glabrous. Tube texture: Pubescent. Color: Petal lobe, when opening, upper surface: Close to 185A to 185B. Petal lobe, when opening, lower surface: More pink than 201C. Petal lobe, fully opened, upper surface: Close to 53A; towards the throat, close to 187A; venation, close to 187B; color becoming closer to 184C to 184D with development. Petal lobe, fully opened, lower surface: Close to 183D; venation, close to 187A to 187B. Throat: Close to 153D; venation, close to 191A. Tube: Close to 195B; venation, close to 187B.

*Calyx*.—Arrangement: One star-shaped calyx tube with five sepals fused towards the base and arranged in a single whorl. Sepal length: About 1.4 cm. Sepal width: About 3 mm. Sepal shape: Lanceolate. Sepal apex: Acute. Sepal margin: Entire. Sepal texture, upper and lower surfaces: Pubescent. Color, upper surface: Close to 137A. Color, lower surface: Close to 137B.

*Peduncles*.—Length: About 2 cm. Diameter: About 1 mm. Angle: About 45° from stem axis. Strength: Strong. Texture: Pubescent. Color: Close to 145A.

*Reproductive organs*.—Stamens: Quantity: About five per flower. Filament length: About 1 cm. Filament color: Close to 145C. Anther shape: Oval. Anther length: About 1 mm. Anther color: Close to 11C. Pollen amount: Scarce. Pollen color: Close to 11B. Pistils: Quantity: One per flower. Pistil length: About 8 mm. Style length: About 6 mm. Style color: Close to 146C. Stigma shape: Round. Stigma color: Close to 146C. Ovary color: Close to 145A. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'USCAL08501' as illustrated and described.

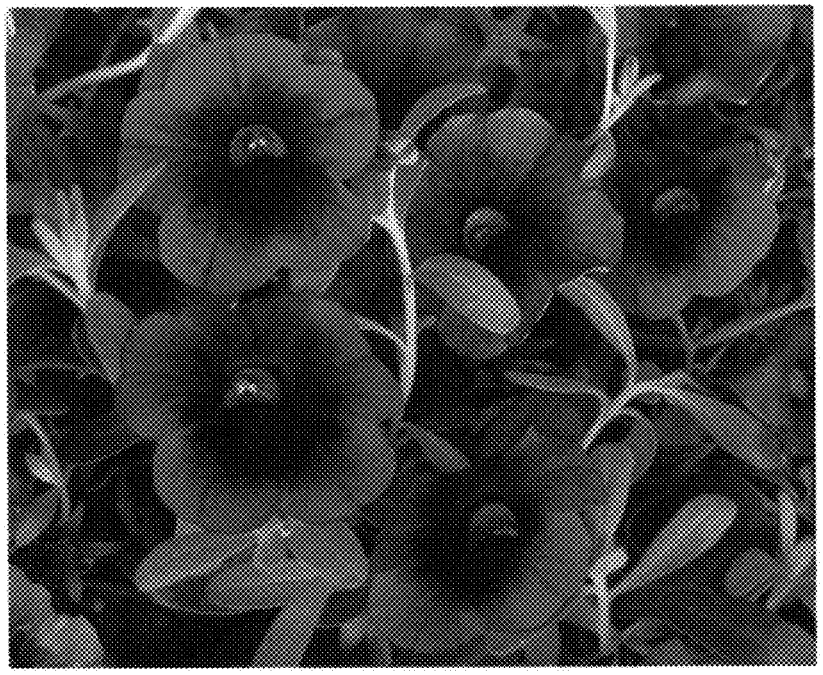
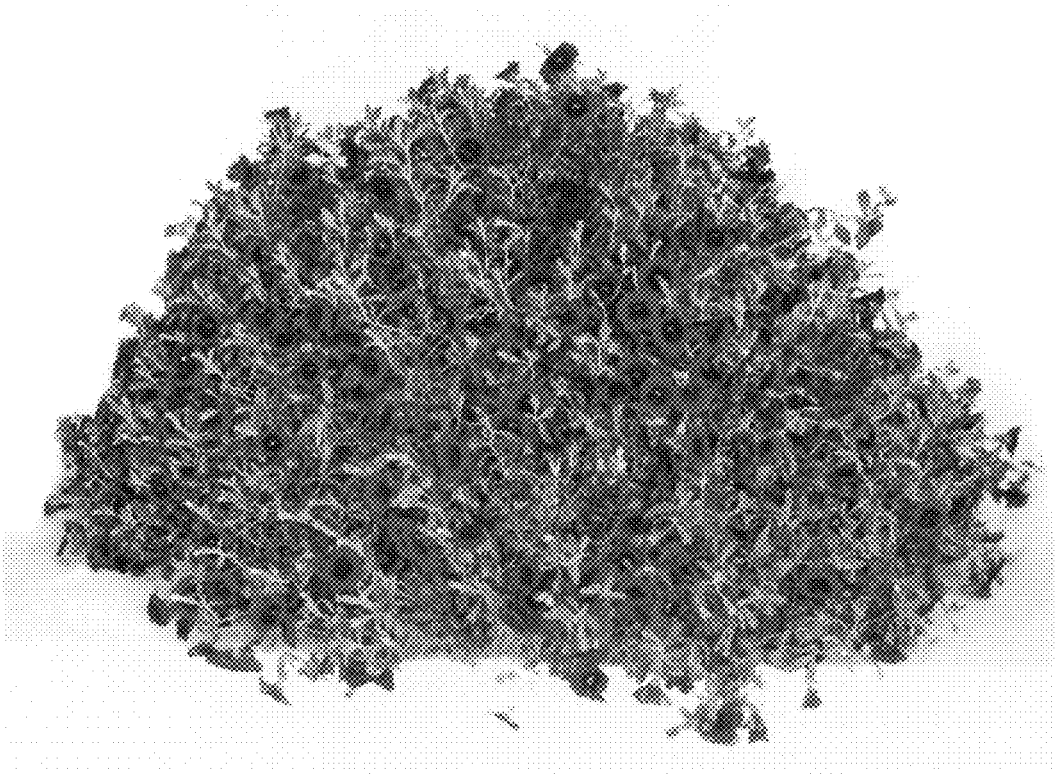

* * * * *